United States Patent [19]

Faccioli et al.

[11] Patent Number: 5,620,449
[45] Date of Patent: Apr. 15, 1997

[54] MECHANICAL SYSTEM FOR BLIND NAIL-HOLE ALIGNMENT OF BONE SCREWS

[75] Inventors: Giovanni Faccioli, Monzambano; Stefano Rossi, Verona, both of Italy; William C. Oppenheim, Short Hills, N.J.

[73] Assignee: Orthofix, S.r.l., Bussolengo, Italy

[21] Appl. No.: 401,094

[22] Filed: Mar. 8, 1995

Related U.S. Application Data

[63] Continuation-in-part of Ser. No. 310,622, Sep. 22, 1994, abandoned.

[30] Foreign Application Priority Data

Jul. 28, 1994 [IT] Italy .................. VR94A0069

[51] Int. Cl.[6] ........................................ A61B 17/56
[52] U.S. Cl. ............................... 606/98; 606/96
[58] Field of Search .................. 606/96, 98, 86, 606/80, 79, 88, 97

[56] References Cited

U.S. PATENT DOCUMENTS

| 5,346,496 | 9/1994 | Pennig | 606/96 |
| 5,433,720 | 7/1995 | Faccioli et al. | 606/98 |

FOREIGN PATENT DOCUMENTS

| 4240277 | 6/1993 | Germany | 606/96 |
| 92/01422 | 2/1992 | WIPO | 606/98 |

Primary Examiner—Guy V. Tucker
Attorney, Agent, or Firm—Hopgood, Calimafde, Kalil & Judlowe

[57] ABSTRACT

A blind-hole locating system wherein a drill jig, which is to be removably attached to the proximal end of a given intramedullary nail, incorporates outrigger structure for support and orientation of one or more drill guides, such that positioning and alignment with one or more bone-screw holes of the nail can be checked and ascertained as a preliminary step, and such that a precise spacer or stabilizer carried by this jig can be known to contact the nail, on an alignment transverse to the nail and to a geometric plane which includes the nail axis and the axis of at least one of the bone-screw holes of the nail, such stabilizer contact being achieved only for the case of correct drill-guide alignment with one or more bone-screw holes. Having thus ascertained that the spacer correctly identifies drill-guide alignment with bone-screw holes, it is only necessary, after installing the nail and connecting the jig to the proximal end of the nail, to make a small local surgical incision through flesh and bone sufficient to enable direct stabilizer contact with the nail, whereupon it is known that the drill guides are in correctly drillable alignment with the targeted bone-screw holes of the installed nail. Drilling and setting of bone screws can immediately proceed in customary manner.

41 Claims, 8 Drawing Sheets

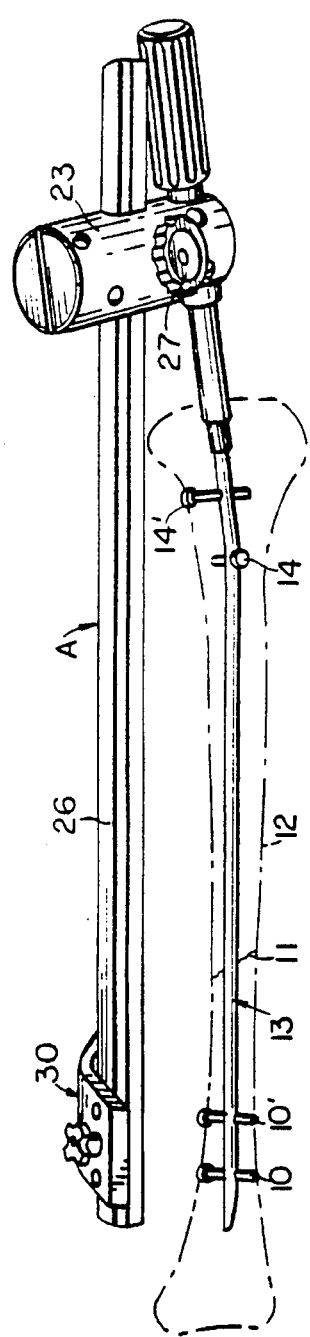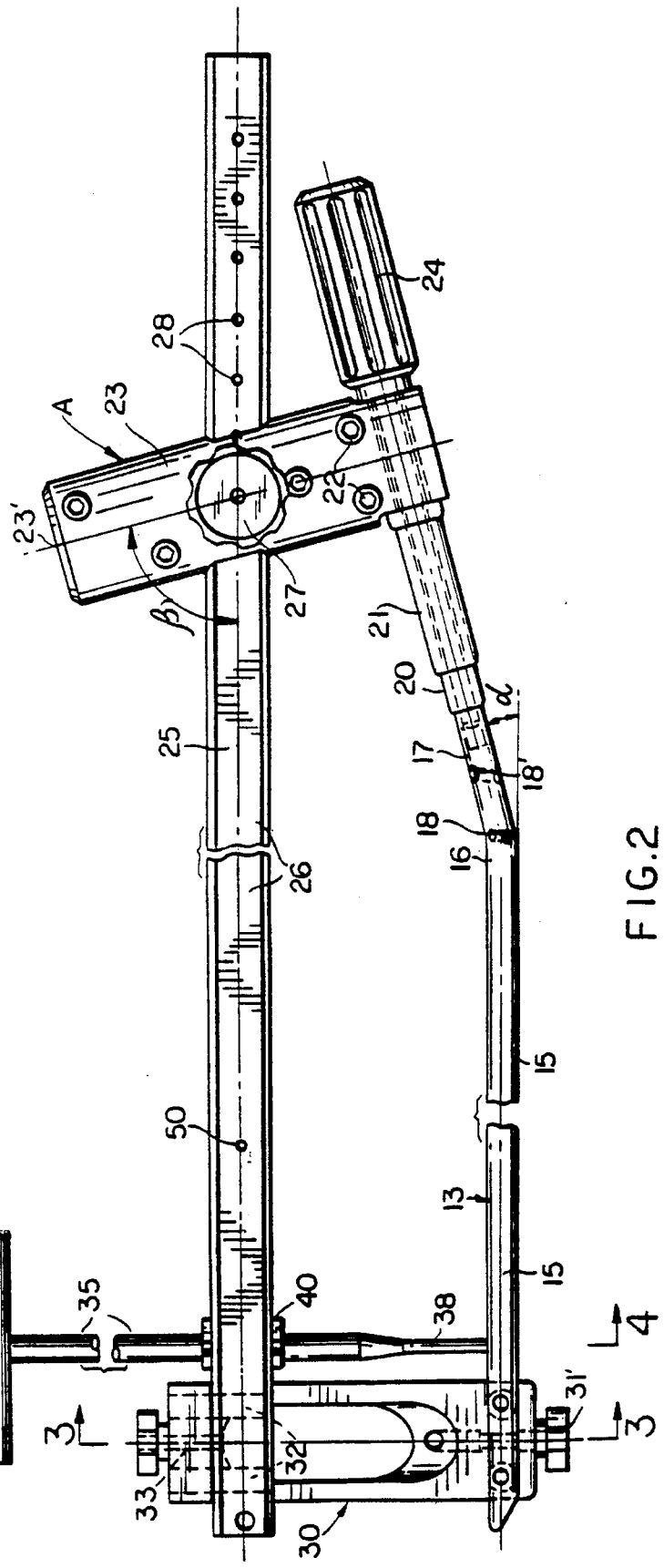
FIG.1
FIG.2

MECHANICAL SYSTEM FOR BLIND NAIL-HOLE ALIGNMENT OF BONE SCREWS

RELATED CASE

This application is a continuation-in-part of application, Ser. No. 08/310,622, filed Sep. 22, 1994, now abandoned.

BACKGROUND OF THE INVENTION

The invention relates to a jig system adapted for connection to an intramedullary nail, wherein the intramedullary nail is implanted in a fractured bone, such as a tibia, the implantation being such as to have the nail extend distally and proximally with respect to the fracture, in reinforcement of fractured parts of the bone that have been re-aligned or merely are to be held in alignment for the course of healing repair.

Intramedullary nails of the character indicated are either solid or hollow, but they are customarily prepared with two spaced parallel holes that extend diametrically across the nail near the distal end of the nail and with two spaced holes of similar nature, but not necessarily parallel, near the proximal end of the nail. These holes are formed to accept bone screws, and when the nail has been installed, its bone-screw holes are said to be "blind" in terms of the bone-drilling alignment that must be achieved. The problem has always been one of assuring correct alignment for drilling to accept a bone screw driven through bone for anchoring passage through the intramedullary nail. The traditional technique for assuring blind drill alignment with the bone-screw holes of an intramedullary nail involves use of x-rays, which of course pose well-known dangers from cumulative exposure; and to assure adequate safety for operating personnel, the use of x-rays is, to say the least, cumbersome, thus contributing to the expense of a good intramedullary-nail installation.

The proximal end of the nail is formed for anti-rotational keyed and detachably fixed connection to jig structure that is intended to aid in orientation of drill guides in the hope of achieving a correct alignment with each drill hole, the customary technique of ascertaining alignment being by use of x-rays.

One of the problems of locating a bone-screw hole in an installed intramedullary nail is the practical fact that the nail may have undergone a slight bend in the course of implantation, so that such holes at the distal end of the nail no longer have precisely the same location with respect to the proximal end, as was the case prior to nail implantation. Thus, any jig structure connected to the proximal end has had to rely on x-rays for assurance of alignment.

In an effort to avoid x-ray dependance in solving the problem of locating blind bone-screw holes in an installed intramedullary nail, U.S. Pat. No. 5,281,224 and pending U.S. application Ser. No. 08/121,762 have proposed magnetic detection, in the scanning displacement of a detection system across the distal region of an installed nail, to locate the central axis of the nail; but in the present state of development, such techniques have been clinically awkward, achieving less than the accuracy that is required.

BRIEF STATEMENT OF THE INVENTION

It is an object of the invention to provide an improved system of blind-hole location for the case of an installed intramedullary nail.

Another object is to meet the above object with a purely mechanical system and technique which does not require use of x-radiation.

A further object is to meet the above objects with a system which enables faster operations, with assurance of correct alignment of bone drilling with the bone-screw holes of an installed nail, particularly at or near the distal end of the nail.

The invention achieves these objects and further features of novelty in a blind-hole locating system wherein a drill jig, which is to be removably attached to the proximal end of a given intramedullary nail, incorporates outrigger structure for support and orientation of one or more drill guides, such that positioning and alignment with one or more bone-screw holes of the nail can be checked and ascertained as a preliminary step, and such that a precise spacer or stabilizer carried by this jig can be known to contact the nail, on an alignment transverse to the nail and to a geometric plane which includes the nail axis and the axis of at least one of the bone-screw holes of the nail, such stabilizer contact being achieved only for the case of correct drill-guide alignment with one or more bone-screw holes. Having thus ascertained that the spacer correctly identifies drill-guide alignment with bone-screw holes, it is only necessary, after installing the nail and connecting the jig to the proximal end of the nail, to make a small local surgical incision through flesh and bone sufficient to enable direct stabilizer contact with the nail, whereupon it is known that the drill guides are in correctly drillable alignment with the targeted bone-screw holes of the installed nail. Drilling and setting of bone screws can immediately proceed in customary manner.

BRIEF DESCRIPTION OF THE DRAWINGS

The invention will be described in detail for preferred embodiments having particular application to a tibial fracture, the description being in conjunction with the accompanying drawings, in which:

FIG. 1 is a simplified perspective view from above and to one side of an intramedullary nail and connected jig structure of the invention, showing distal and proximal nails that have been installed in a fractured tibia, the tibia being shown in phantom outline, and flesh profiles being omitted in the drawing;

FIG. 2 is an enlarged view in side elevation of the jig and nail of FIG. 1, partly broken-away to provide greater detail of distal and proximal coaction between nail and jig components;

Figure 3:
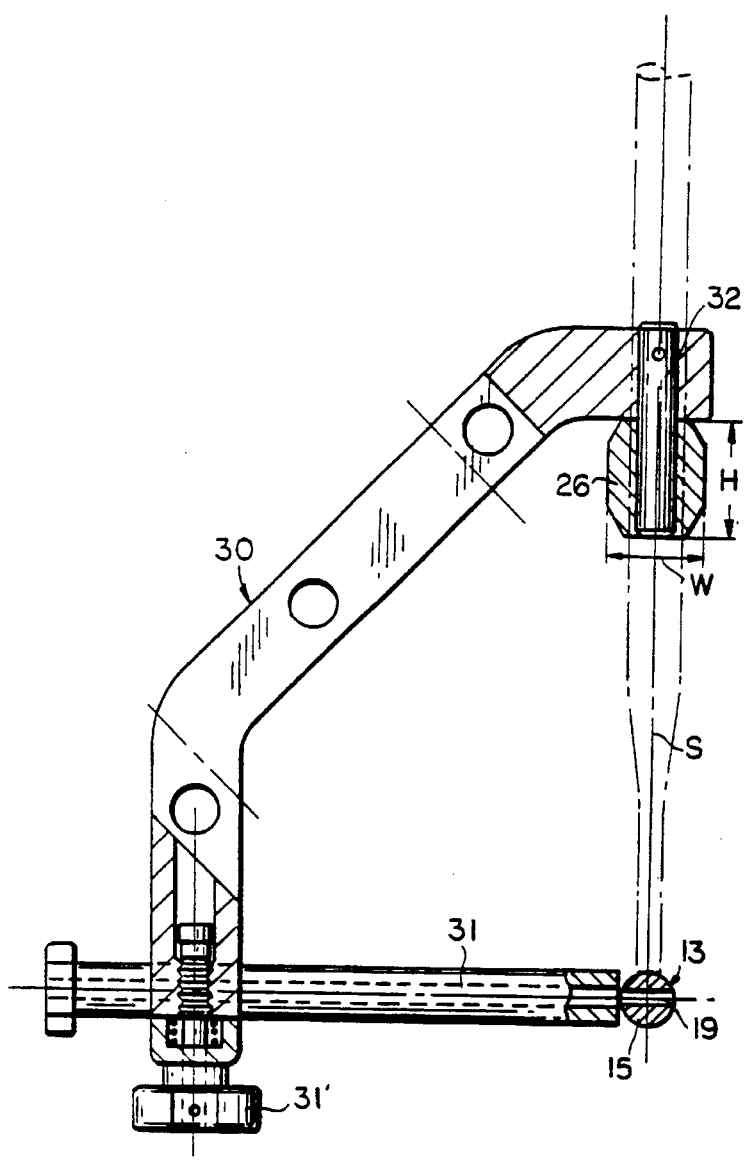
FIG. 3 is a further enlarged section of distal outrigger structure of FIG. 2, taken at 3—3 of FIG. 2.
Figure 10:
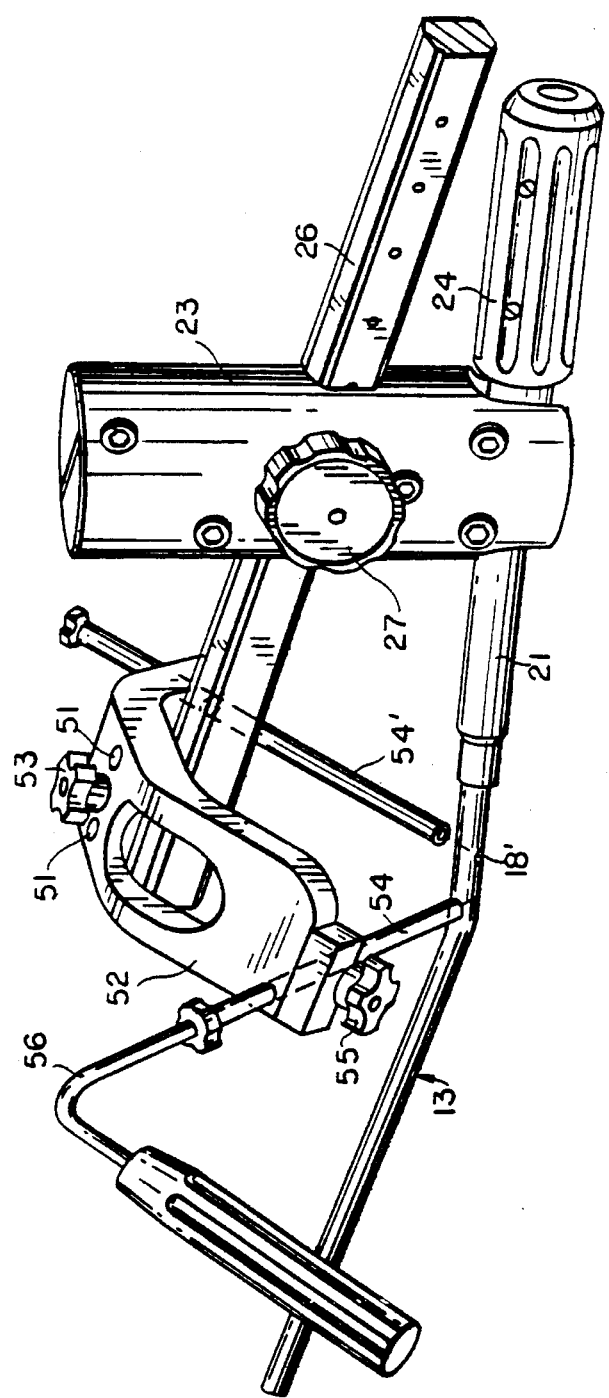
Figure 11:
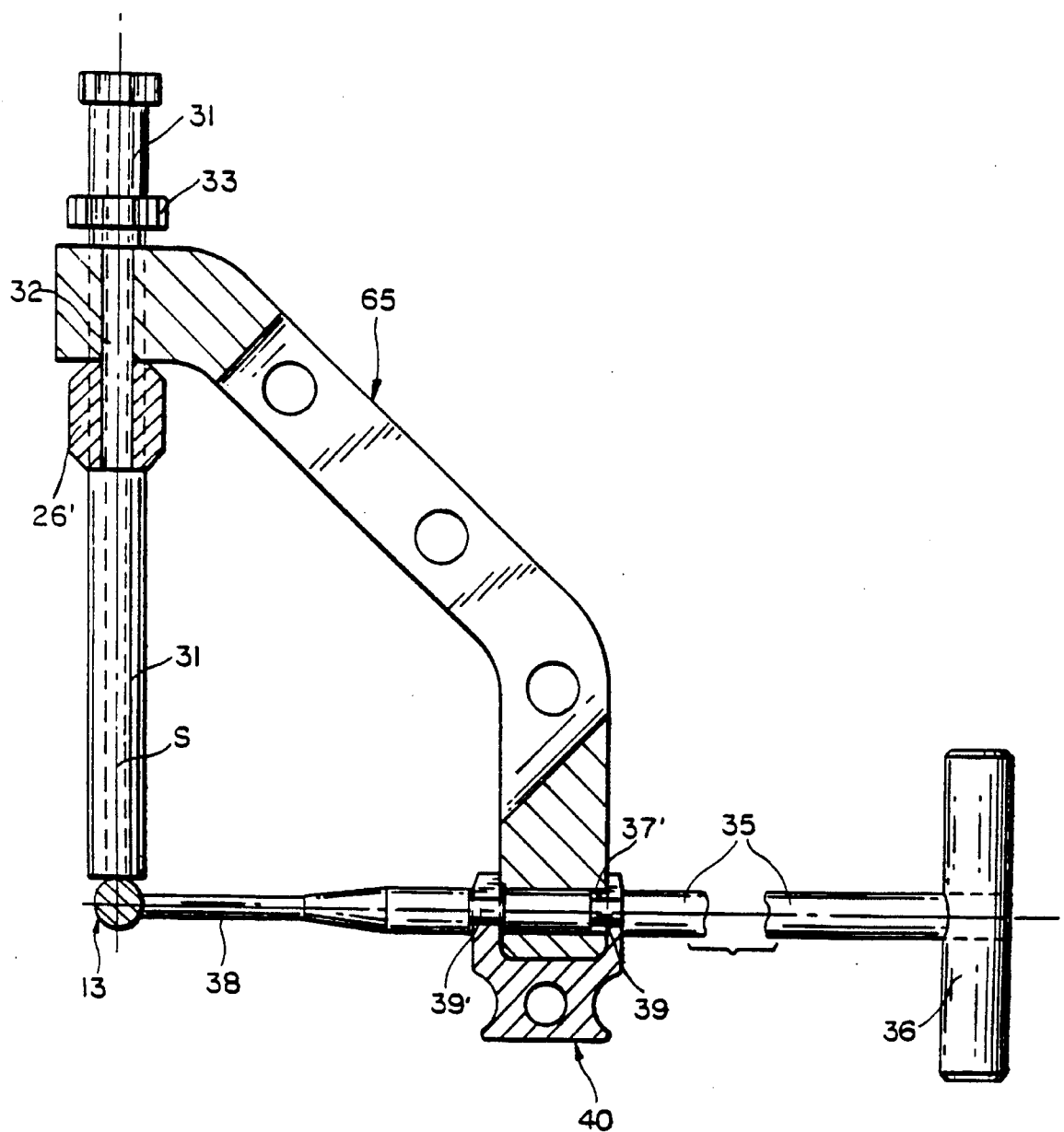
Figure 12:
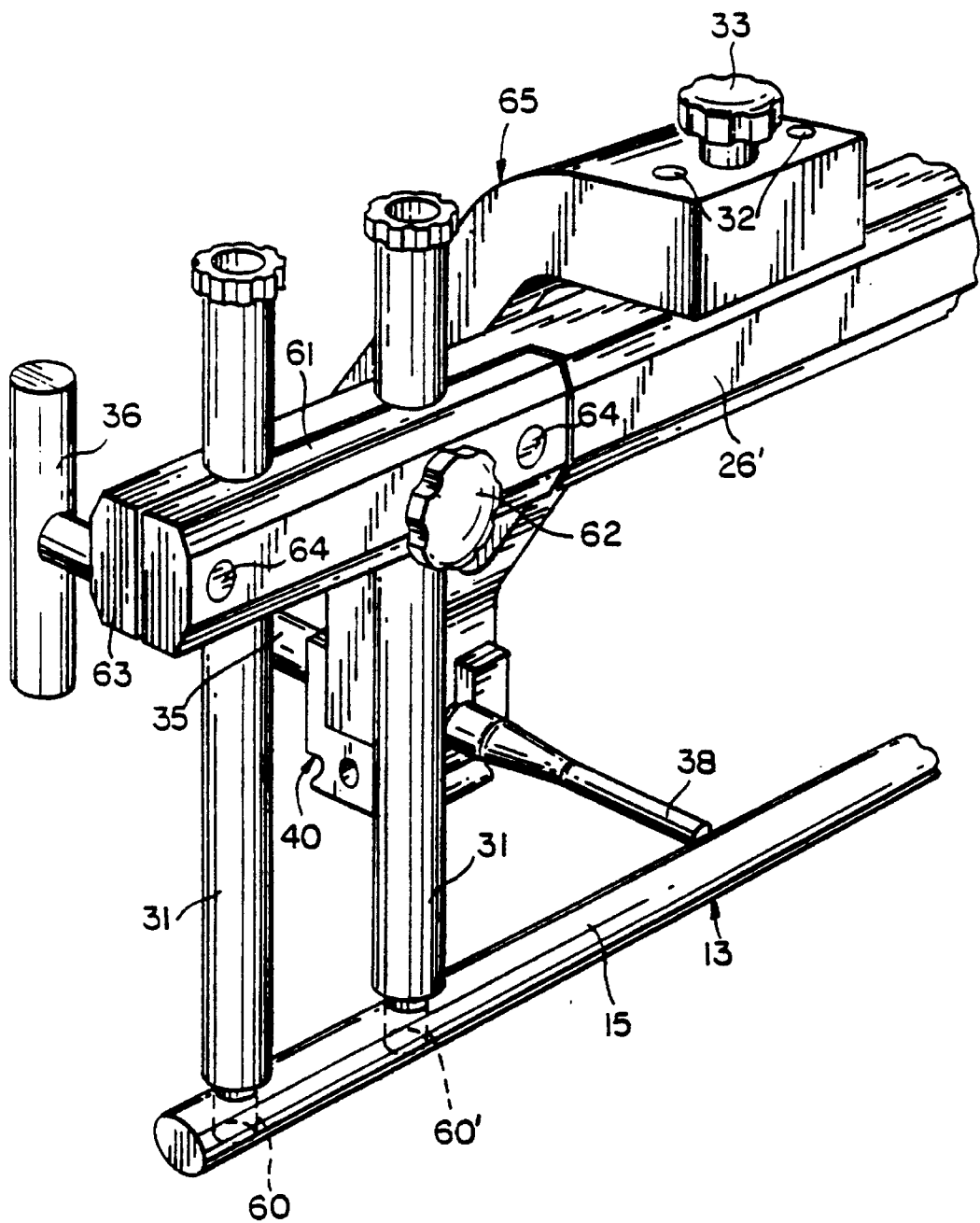

3 nally spaced bone screws at mutually divergent orientations through bone, at the proximal end of the intramedullary nail of FIG. 2;

FIG. 10 is an enlarged view in perspective to show greater detail of outrigger, drill-guide and jig structure at the proximal end of the system;

FIG. 11 is a view similar to FIG. 3 to show a modification, the viewing aspect being opposite to that of FIG. 3; and FIG. 12 ms a perspective view of the modification of FIG. 11, taken from a three-quarter aspect on the distal end of the modification.

Figure 13:
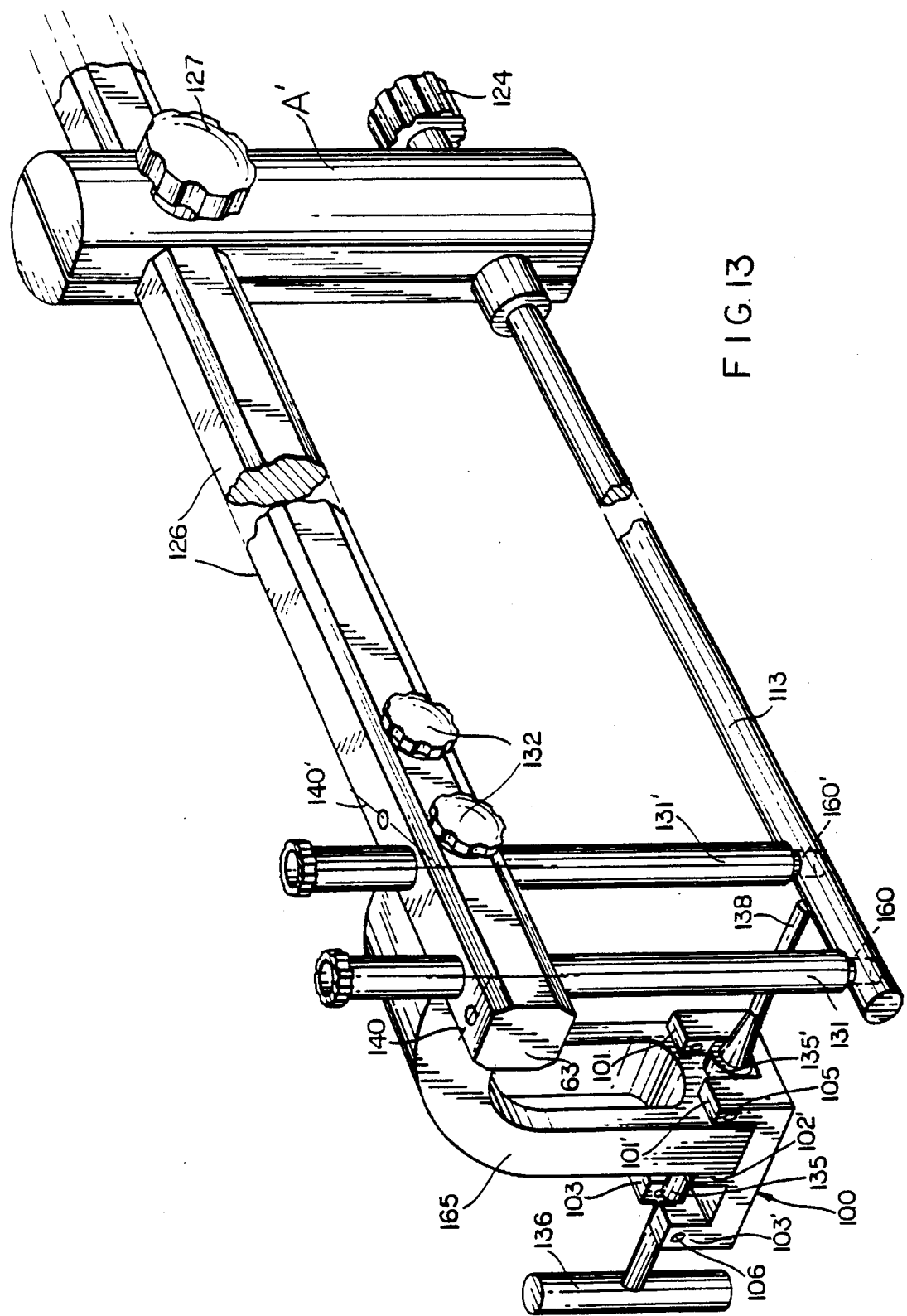
Figure 14:
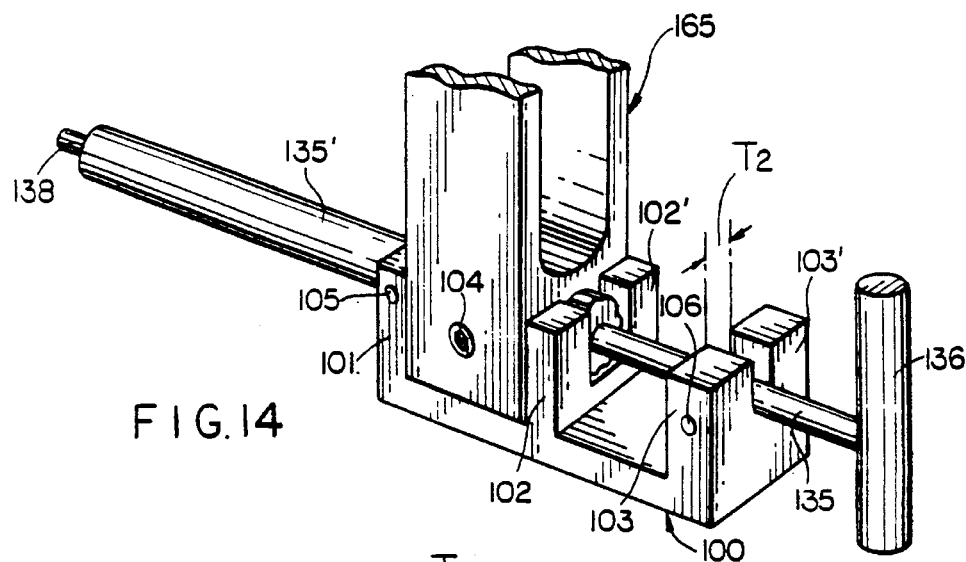
Figure 15:
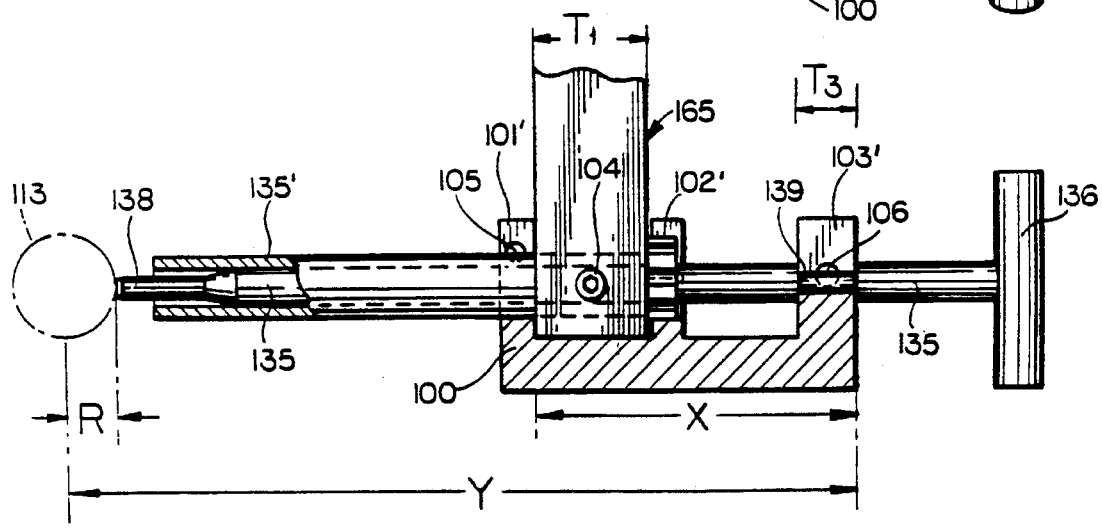

FIG. 13 is a perspective view of a jig that is similar to FIG. 2, for the case of modified structure that is specifically useful in application to a fractured femur;

FIG. 14 is a perspective view similar to FIG. 12, showing the distal end of outrigger structure of FIG. 13; and FIG. 15 is a fragmentary side elevation in partial section for stabilizer-rod positioning structure for the embodiment of FIGS. 13 and 14.

DETAILED DESCRIPTION

In FIG. 1, the invention is seen as jig structure, generally designated A, after having completed its job of correctly aligning, drilling and enabling installation of two bone screws 10, 10' at a location distal to a fracture 11 in a tibia 12 which has been reinforced by an elongate intramedullary nail 13; the bone screws 10, 10' will be understood to pass through spaced parallel bone-screw holes extending diametrically through nail 13. Two further bone screws 14, 14' are shown installed near the proximal end of the nail; the drilling for accommodation of bone screws 14, 14' is accomplished pursuant to later description, in connection with FIGS. 9 and 10.

Figure 9:
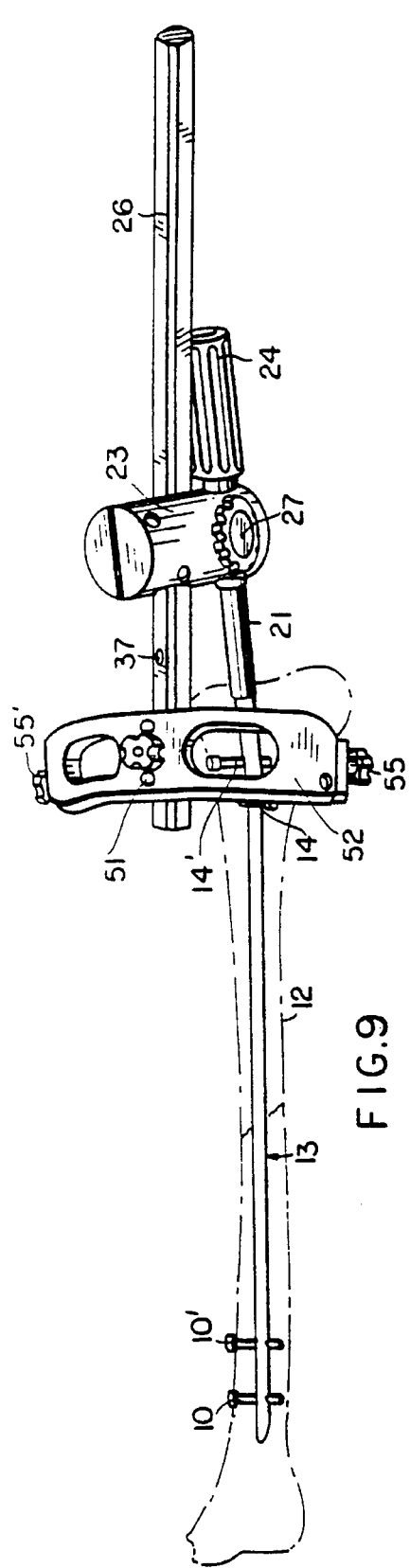
FIG. 9 is a view similar to FIG. 1, for the same jig but different outrigger structure used to install two longitudi-

The jig structure A comprises a plurality of separably and adjustably connectable components, better seen and identified in FIG. 2, where the intramedullary nail 13 is shown to comprise an elongate straight distally extending portion 15 for most of its length, there being a short bend 16 at an acute angle α near the proximal end 17 of the nail; two spaced diametrically extending bone-screw holes 18, 18' in the bent proximal end 17 are for accommodation of the screws 14, 14' to be described later in connection with FIGS. 9 and 10. The bend 16 between otherwise straight distal (15) and proximal (17) portions of nail 13 will be understood to define a single plane of symmetry which will be referred to as the sagittal plane, containing the bent axis of the nail; and the distal bone-screw holes (as at 19 in FIG. 3) for bone screws 10, 10' will be understood to be normal to the sagittal plane.

The proximal end of nail 13 has keyed fit to jig A via the chuck 20 of an elongate locking rod 21, which is clamped by bolts 22 between front and back halves of a handle 23. A knob 24 is rotatable to releasably secure the engagement of jig structure in accurately keyed relation to the proximal end of the nail. As thus clamped and engaged to the nail, the central axis 23' of handle 23 extends at a right angle to the axis of the proximal end 17 of the nail, and this central axis 23' lies in the sagittal plane of the connected nail.

Confronting faces of the bolted halves of handle 23 are grooved to establish a central axis 25 for slant-guided alignment of an elongate guide bar 26, wherein the central axis 25 of bar 26 intersects the central axis 23' of handle 23 and wherein axis 25 is also contained within the same sagittal plane of the nail; the slant angle β of intersection of

4 axes 23', 25 is the complement of angle α, so that guide bar 26 is necessarily parallel to the elongate distal end portion 15 of the intramedullary nail. The cross-sections of guide bar 26 and of the handle grooving to accommodate bar 26 are non-circular and preferably rectangular, with a height dimension H which exceeds its width dimension W, suitably by about 25 percent, as seen in FIG. 3, wherein corners of the section are bevelled. A locking knob 27 carried by handle 23 includes a dowel portion which is selectively enterable in a given one out of a plurality of spaced transverses openings 28 in bar 26, the selection among openings 28 being dependent upon the length of the particular intramedullary nail 13 selected for implantation. It is preferred that openings 28 be of limited depth in bar 26 and that the bottom of each opening 28 be conical, so that with a conically-tipped dowel secured by locking knob 27, the cone-to-cone engagement will assure an accurate, play-free location of handle 23.

Distal outrigger structure 30 is removably carried by guide bar 26 near the distal end of bar 26, to provide such lateral and downward offset of its lower end, from bar 26 and away from the sagittal plane, as to enable precise spaced parallel orientation and clamping of two elongate drill guides 31, in alignment with each of the respective bone-screw holes 19 near the distal end of the nail 13, all as best seen in FIG. 3; a knob 31' enables clamped positioning of the drill guides 31 to the laterally offset end of outrigger 30. For accuracy in establishing the indicated offset, the upper end of outrigger 30 mounts two spaced dowels 32 having precision entry in vertical guide bores through guide bar 26, and outrigger 30 is securely clamped by a knob-driven locking bolt 33 engaged to a suitably tapped vertical bore in guide bar 26, located between the two dowel pins. The vertical orientation of dowel pins 32 and of the guide bar 26 symmetrically with respect to the sagittal plane S of nail 13 is clear from FIG. 3 and its legends.

A further important component of the jig of FIG. 2 is an elongate spacer or stabilizer rod 35, having a manipulating handle 36 at its upper end. For most of its length, rod 35 is of constant diameter for guided stability in a vertical bore 37 in guide bar 26, in spaced adjacency to the mounting of outrigger 30. At its lower end, the diameter of rod 35 is reduced to define a cylindrical portion 38 of length L which, as will later be explained, must be passed through a small surgical incision of flesh and local drilling of bone, to permit lower-end contact, as shown, with nail 13.

The stabilizer rod 35 is designed for precise positioning of its lower end with respect to guide bar 26 when in contact with nail 13, namely, when each drill guide 31 is truly aligned with a bone-screw hole 19 in the nail. To this end, spaced upper and lower circumferential grooves 39, 39' are formed in rod 35, and each of these grooves straddles upper and lower intercepts of rod 35 with the respective upper and lower faces of the rectangular section of guide bar 26. A shim 40 in the form of a clip is laterally applicable to guide bar 26, with provision for entry into the respective grooves 39, 39', to thereby limit the extent to which the lower end of stabilizer rod 35 can be projected toward nail 13. More detail as to shim 40 is obtained by further reference to the respective views of FIGS. 5, 6, and 7.

Figure 4:
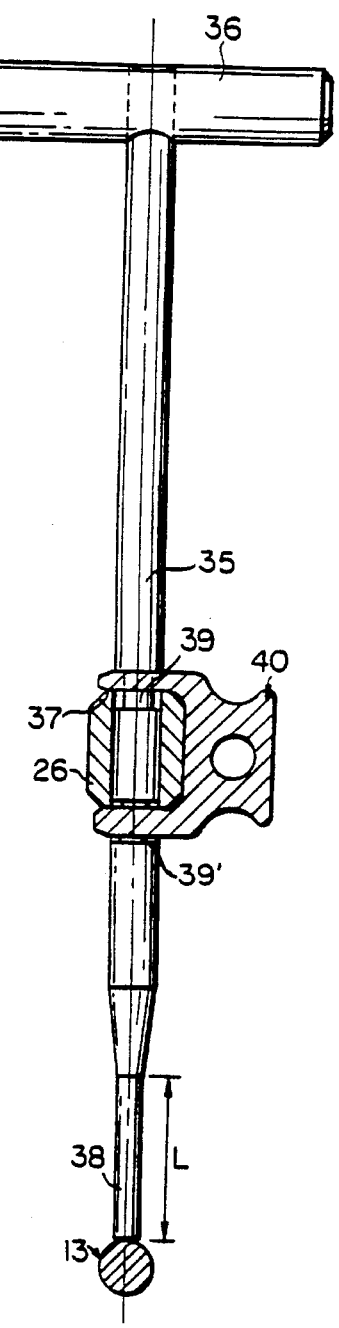
FIG. 4 is another view, to the scale of FIG. 3 and in partial section taken at 4—4 of FIG. 2, to show stabilizer structure of FIG. 2.
Figure 5:
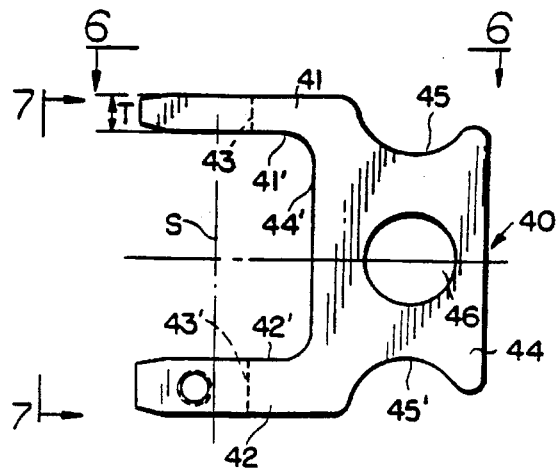
FIG. 5 is a view in side elevation and to a still-further enlarged scale, for a nail-size compensation component of the jig in FIG. 2.

As viewed from the aspect shown in FIG. 4, and as more particularly seen in FIG. 5, the shim 40 is of generally C-shape, being characterized upper and lower jaws 41, 42 which have vertically aligned side-entry slots 43, 43', of width less than the diameter of rod 35. Jaws 41, 42 extend integrally from a body 44 having upper and lower finger-grip recesses 45, 45' and also having a central through-hole 46 for tool-assisted removal from guide bar 26, if necessary. Innerwall surfaces 41', 42', 44' of the C-shape are formed for unambiguous stabilizing engagement to corresponding sides of the section of guide bar 26. A spring detent 47 has snap-engagement to the rod groove 39' upon application of shim 40 to guide bar 26, when rod 35 is positioned as shown in FIG. 4 to accept entry of the jaws 41, 42 into the respective grooves 39, 39'. When thus engaged, with the bottoms of grooves 39, 39' nested in the arcuate closed ends of slots 43, 43', the central axis of stabilizer rod 35 will be in the alignment marked S in FIG. 5, signifying rod-35 inclusion in the same sagittal plane as has been elsewhere indicated for other components of the jig system.

Figure 6:
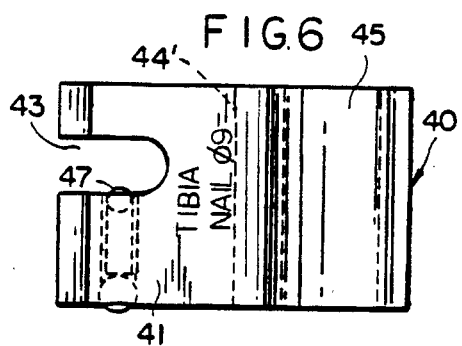
FIG. 6 is a top view of the nail-size compensation component of FIG. 5.
Figure 7:
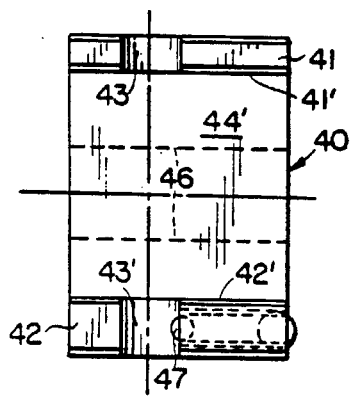
FIG. 7 is a left-end view in elevation of the component of FIG. 5.

The word "shim" has been used for the component just described in connection with FIGS. 5, 6 and 7 because the thickness "T" shown in FIG. 5 is uniquely designed to position the lower end of stabilizer rod 35 at contact with nail 13, when drill guides are correctly aligned with respect to the distal bone-screw holes of the nail. But the precise thickness T will apply only for one of a series of possible section diameters of intramedullary nail. In the form shown, a 9-mm diameter nail 13 calls for a bottom-positioning limit for rod 35 that is unique, and therefore the thickness T in FIG. 5 is unique for tibia use with a 9-mm diameter nail. The unique limit of downward projection of the bottom or tip end of rod 35 occurs when the upper surface of jaw 41 interferes with the upper shoulder or wall of upper groove 39 of rod 35. Any further attempted depression of rod 35 will drive the shim thickness T of jaw 41 squarely against the flat upper surface of guide bar 26, tending to bend bar 26 if the force is great enough, but never spoiling the correctly spaced distance of nail 13 beneath bar 26, it being noted that any bend of bar 26 is not only accompanied by correctly spaced deflection of nail 13 but also by similarly correct displacement of the drill guides carried by outrigger 30.

It will be helpful briefly to outline steps taken with the described jig A to assure quick and accurate drilling of bone for distal bone-screw anchorage to an installed intramedullary nail 13. First, an intramedullary nail 13 should be selected for nail diameter and overall length to serve the surgeon's purposes in the light of a particular fracture 11. Suitable surgery is performed to assure entry of the selected nail in direct alignment with the medullary cavity, but first it is recommended that, at least for distal-drilling purposes, the selected nail be assembled to the jig A to ascertain correct length adjustment (via dowel knob 27) at the correct one of the predrilled locations 28 along guide bar 26. Outrigger 30 should be assembled to bar 26, along with two drill guides 31, securely setting the knob of bolt 33 and of the drill-guide clamp 31'. Additionally, stabilizer rod 35 should be inserted in bore 37 in guide bar 26 and the correctly selected shim fitment 40 should be assembled with its upper and lower jaws engaged in the upper and lower circumferential grooves 39, 39' of rod 35. Depression of rod 35 may or may not be necessary to bring rod 35 into contact with nail, at which point visual sighting or trocar passage down each drill-guide bore should confirm correct alignment with the respective bone-screw holes in nail 13. That done, all is in readiness for a correctly aligned drilling procedure, which of course must be preceded by correct surgical insertion of the intra-medullary nail 13 in the fractured bone.

After installing nail 13, whether the nail be solid or hollow, and with the handle 23 of the jig (A) locked in its keyed connection to the proximal end of the nail, the guide bar 26 should be introduced into the handle 23, moving the same to its pre-established point for locking-screw retention via knob 27 at one of the length-selection bores 28 in guide bar 26; for convenience, the upper surface of the guide bar 26 will be understood to have been inscribed with unit-length markers at unit spacing, corresponding to the length of intramedullary nails of an available set, and it will be further understood that engraved length designations, such as 280, 300 . . . in increments of 20-mm up to 400-mm, may be inscribed adjacent successive length markers, as the same may have been available from which to have selected nail 13. Such numerical inscriptions alongside successive length markers that are readable, as at bar-26 emergence from guidance through handle 23, enable the surgeon to make fast and correct length adjustment and locking of bar 26, in support of the distal operations to be performed.

The distal outrigger 30 is next mounted on guide bar 26 so that it is positioned on the medial side of the tibia, and the screw guides 31 are inserted into the outrigger to determine proper locations for the incisions. An incision is then made beneath each screw guide, and the medial cortex is exposed in each incision by blunt dissection, taking care to avoid entrapment of or damage to the saphenous nerve and vein. The guides 31 are then advanced until they are in contact with the medial cortex. The clamp 31' on outrigger 30 is then tightened to hold the screw guides firmly in place.

Figure 8:
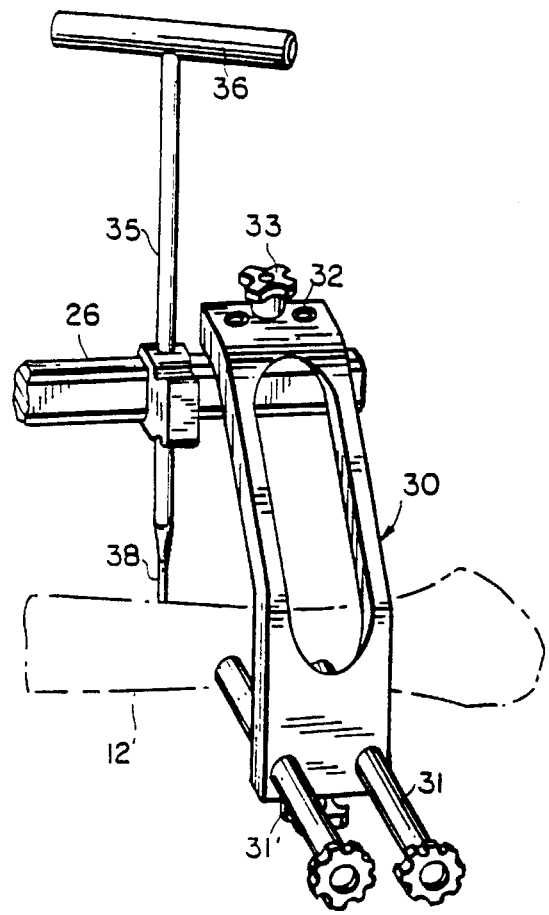
FIG. 8 is a perspective view of coacting parts of the distal end of FIG. 2, in readiness for correctly aligned drilling for bone-screw anchorage to blind holes of the installed intramedullary nail of FIG. 2.

Before any bone-screw holes are drilled, the system is stabilized in exact alignment. To this end, a drill guide (not shown) is inserted into the vertical bore 37 which has been previously described for stabilizer-rod (35) accommodation; an incision is made in the skin directly beneath this vertically oriented drill guide, and the anterior tibial cortex is exposed by blunt dissection. The drill guide is then advanced until its teeth are engaged onto the anterior border of the tibia; whereupon, a drill bit (e.g., of 4-mm diameter) is used to drill only the anterior cortex, and the drill bit is then removed. At this stage, because of the shape of the drill bit, the hole in the bone is tapered, so that a square-ended 4-mm T-handled reamer (not shown) is passed down the drill guide, to complete the hole down to the nail, and intervening debris is removed. The hand reamer and vertical drill guide are now removed and are replaced by entry of stabilizer rod 35 in vertical bore 37, the same being inserted to the point of reduced end (38) passage through the drilled hole in the cortex and into contact with nail 13. The stabilizing rod 35 must be set in the correct position for the particular diameter of nail 13, and this is achieved by inserting the correct U-shaped spacer (with shim thickness T) 40 over guide bar 26, so that its forks engage into the two circumferential grooves 39, 39' of the stabilizer rod. The correct shim is observable via inscription of nail diameter on the exposed upper face of shim 40, as indicated by the engraved marking "NAIL φ9"0 shown on this face in FIG. 6, meaning "nail diameter 9-mm". The outrigger 30, its screw guides engaged to the bone, and its stabilizer rod 35 engaged to the nail, now have the relationship shown in FIG. 8.

An assistant to the surgeon now presses on the T-handle 36 of the stabilizer rod, thus pressing its lower end or tip into loaded contact with the nail 13. This procedural step will be seen to achieve the following:

1. The surgeon is assured that the distance between the nail and the guide bar is precisely what it was checked out to be prior to nail insertion in the medullary canal, and this fact also allows for take-up of any bending of the nail in the sagittal plane, thus maintaining and assuring alignment of the distal drill-guide (31) targeting of bone-screw holes 19 in the nail; and 2. The guide bar 26 and outrigger 30 are stabilized, so that the surgeon has a secure platform for drilling distal holes in the bone. Those skilled in the art of setting bone screws through correctly drilled "blind" distal holes in bone should not need further instruction, but it is perhaps well to review successive steps that are recommended for drilling and distal locking, as follows:

(i) The surgeon's assistant should maintain constant gentle downward pressure on the T-handle of stabilizer rod 35, throughout the procedure which follows, as far as step (x) below.

(ii) A 4-mm drill guide is inserted into one of the guides 31, and is gently tapped to engage its distal-end teeth in the medial cortex.

(iii) A drill stop is locked to a selected 4-mm drill bit at the proximal end.

(iv) The drill bit is inserted into the drill guide, down to the bone, with the drill bit chucked to a hand-held electric drill, before the drill is started.

(v) The surgeon now drills steadily through the medial cortex, and stops the drill when the second cortex is reached.

(vi) The drill stop is moved proximally until it is 5-mm above the top of the drill guide, and is locked into place. This resetting of the stop represents an allowance for the thickness of the second cortex.

(vii) Drilling now continues through the second cortex. The drill stop prevents damage to the tissues beyond the bone, and also provides a method of estimating the correct length of locking screw.

(viii) The drill bit is removed with the drill guide.

(ix) An angled trocar is selected and now inserted into the screw guide, so that it passes through the nail, and engages in the far cortex. The trocar has now stabilized the position of the guide bar and outrigger.

(x) Now that the screw-guide alignment is held by the trocar, the assistant may release the pressure on the T-handle of stabilizer rod 35.

(xi) The locking screw length, from the base of the screw head, is determined by measuring the amount of drill bit protruding from the drill guide.

(xii) The drill stop is now replaced at the proximal end of the drill bit, in readiness for repeating the drilling procedure for the other one of the distal bone-screw holes of nail 13.

(xiii) The second locking hole is now drilled, using exactly the same technique.

(xiv) The length of the second locking screw is determined as before.

(xv) A locking screw of correct length is now inserted into the second guide 31, and pushed through the bone, as with a suitably marked T-wrench, until the thread engages with the medial cortex. The locking screw is now turned clockwise, exerting gentle pressure, until a mark on the shaft of the T-wrench reaches the top of the screw guide. [It is important not to continue turning after this position is reached, otherwise the thread in the bone will be stripped.]

(xvi) The trocar is removed from the first guide 31, and the same technique is followed for the insertion of the second locking screw, after which both guides 31 are removed by loosening the guide-locking knob 31'.

(xvii) A check should now be carried out with an Image Intensifier or by x-ray to confirm that both screws have passed through the nail and to confirm that the reduction has been maintained.

(xviii) The distal outrigger 30 and the T-handled stabilizer or spacing bar 35 are now removed.

Having completed first the distal installation of bone screws, and before proximal locking, the fracture should be examined by x-radiation to determine whether there is any remaining distraction. If there is, conventional techniques are known, whereby to reduce the distraction, so that proximal locking can proceed.

For proximal-locking use of the jig A, and with the distal outrigger 30 and stabilizer rod 35 removed, it is first necessary to reset guide bar 26 in handle 23, by setting the locking knob 27 so as to engage and lock handle 23 to bar 26 via another locating bore 50 near the distal end of bar 26. This will expose the two dowel-engageable bores at the distal end of bar 26, for acceptance of the two locating dowels 51 of a proximal outrigger structure 52. In the case depicted, the two bone-screw holes 18, 18' for proximal bone-screw anchorage are on orthogonally related axes that are longitudinally spaced from each other; the proximal outrigger 52 therefore straddles guide bar 26 via its central body region, with its dowel pins 51 projecting downward from its central body region, and with provision for locking the outrigger to the guide bar by way of knob-driven means 53. Drilling access on the respective axes of these holes 18, 18' is at equal and opposite 45° inclinations with respect to the sagittal plane of nail 13, and therefore the proximal outrigger 52 provides at one of its ends for clamped mounting of a drill guide 54 in alignment with hole 18, and, at the other of its ends, for clamped mounting of a second drill guide 54' in alignment with the other proximal bone-screw hole 18'. Clamping access for setting the drill guides 54, 54' is identified at knobs 55, 55' in FIGS. 9 and 10.

Procedurally, it is not necessary for the surgeon to check out his jig settings of drill guides prior to nail 13 implantation in the fractured bone, as long as the surgeon has become familiar enough to rely on proper use of correct accessories, such as the distal outrigger 30 and the proximal outrigger 52 for a given nail 13. However, before the surgeon has become that familiar with the jig and its proper use, it is well that he additionally check out the coordination of events and relationships at the proximal drilling alignments, as well as the distal drilling alignments, all prior to implantation of nail 13 in the tibia. FIG. 10 shows the relation of parts, for such checking at the proximal drilling sites, prior to nail 13 implantation. Not only does FIG. 10 show that each of the drill guides 54, 54' may be checked for accuracy of registration with the respective proximal bone-screw holes 18, 18', but FIG. 10 additionally shows use of a trocar 56 inserted in one (54) of the drill guides and into stabilizing entry of the aligned bone-screw hole 18 (not visible in FIG. 10, but shown in FIG. 2).

Use of the proximal-locking feature of the jig for proximal drilling is very much as for the case of distal drilling although there is no need for a stabilizer rod 35 or its equivalent, since proximal drilling is so close to the location of jig connection.

After locking the pin or knob 27 to the proximal reference location 50 on guide bar 26, the proximal outrigger 52 is mounted and locked to bar 26, and two screw guides 54 and 54' are clamped at 55, 55' to locate proper sites for the incisions. Two incisions are made, one antero-lateral and one antero-medial, and the tibial cortex is exposed in each case by blunt dissection. The screw guides 54, 54' are advanced down to the cortex and locked in position via clamp knobs 55, 55'. A drill guide is inserted into one of the screw guides, and tapped gently to engage its distal teeth into the cortex. The drill bit is pushed down to the bone, and pressed against the cortex before drilling begins. Further procedures track those described for distal locking. The bone screws are inserted after each hole is drilled, and their length is determined, as described for distal insertion of bone screws.

The modification of FIGS. 11 and 12 illustrates that the invention is also applicable to use of intramedullary nails wherein the axes of spaced parallel bone-screw holes 60, 60' for distal-end fixation to bone are in what may be called the sagittal plane, whether the nail is of bent or straight configuration, the point being that when the proximal end of the nail is keyed in its chucked connection to handle 23, the guide bar, here identified as 26', is parallel to the straight portion 15 of the intramedullary nail. The axes of the straight portion 15 of the nail, and of the jig guide bar 26', and of the bone-screw holes 60, 60' are thus all in the sagittal plane, marked S in FIG. 11.

Since the drilling for bone-screw alignment with nail holes 60, 60' must now also be in the sagittal plane, the distal end of guide bar 26' is seen to provide for the releasably clamped mounting of drill guides 31 for such drilled alignment. Specifically, the distal end of bar 26' is so devised that a clamp block 61 may be clamped via knob actuation at 62 to support the precise spaced parallel relation of two drill guides 31. To this end, the confronting vertical faces of block 61 and of the uncut remainder 63 of the distal end of bar 26', are formed with matching cylindrically arcuate concavities for drill-guide support, and guide pins or dowels 64 carried by block 61 will be understood to have precision location and guidance in corresponding bores (not shown) in the distal-end portion 63 of bar 26'.

An outrigger 65 is generally as described for the outrigger 30 of the first embodiment, in that it has spaced parallel guide pins 32 and a locking knob 33 for accurate and secure outrigger mounting to the upper surface of guide bar 26'. However, the laterally and downwardly offset other end of the outrigger is devised for guidance and selective positioning of a spacer or stabilizer rod 35 in alignment with the central axis of the distal nail portion 15 and perpendicular to the sagittal plane. For this purpose, the same spacer rod 35 (with its spaced grooves 39, 39' is again used for guidance in a bore 37' in the offset end of the outrigger, and a U-shaped shim fitment 40 is selected for assurance that when rod 35 is pressed into mechanical contact with nail 13, it can be known for sure that drill guides 31 are precisely aligned with the bone-screw holes 60, 60' of the nail.

In use of the embodiment of FIGS. 11 and 12, the same procedures outlined above for distal-end use of the device of FIG. 2, will be seen to be equally applicable, except for the fact that spacer bar (35) and drill-guide (31) orientations are reversed in their respective references to the sagittal plane S.

The embodiment of FIGS. 13 to 15 is in many respects similar to that of FIGS. 11 and 12, except that the embodiment of FIGS. 13 to 15 is of specific utility in the blind-hole drilling of a fractured femur, wherein the intramedullary nail 113 is straight, with distal transverse bone-screw holes 160, 160' which are on parallel axes that are perpendicular to the central axis of nail 113 and thus determine a first geometric plane of symmetry. The handle A' has selectively locked and keyed connection to the proximal end of nail 113; handle A' extends perpendicular to nail 113 within the plane of symmetry, and handle A' is also perpendicular to elongate guide-bar structure 126, with means 127 whereby to selectively clamp structure 126 (i) in the indicated plane of symmetry and parallel to nail 113, and (ii) with such distally offsetting projection of structure 126 as to position its two drill guides 131/131', in potential (if not actual) aligning registration with the bone-screw holes 160, 160' of nail 113. Set screws on inclined axes 140/140', and accessible via the upper surface of jig bar 126, will be understood to provide adjusted axial positioning of drill guides 130/130', respectively.

The distal end of bar structure 126 is shown carrying the upper end of outrigger structure 165 which has a vertical-plane mounting face that is in clamped abutment with one of the vertical faces of the constant cross-section of guide-bar structure 126, being clamped by knob-headed bolts 132 which seat against the opposite vertical face of structure 126. It will be understood that bolts 132 have smooth cylindrical dowel-like fit to transverse bores in bar structure 126 and that only their threaded distal ends engage threaded bores in the confronting upper end of the outrigger structure 165. The lower (and laterally offset) end of outrigger structure 165 has a guide bore on an axis perpendicular to the axis of nail 113 and also perpendicular to the indicated first geometric plane of symmetry, being shown to mount a guide sleeve 135' for slidable guidance of a stabilizing rod 135. Rod 135 has a manipulating handle 136 at its proximal end, and a reduced distal end 138 for stabilizing contact with nail 113.

Finally, as best seen in FIGS. 14 and 15, a spacer element 100 has a body with three pairs of upstanding feet 101/101', 102/102', and 103/103', which enable precise positioning of the distal end 138 of rod 135, specific to the outer radius of the nail 113 it is to abut. The first and second pairs of feet 101/101' and 102/102' will be understood to be spaced at distance $T_1$ for accurate friction fit to the opposing parallel faces of outrigger 165, at guide-sleeve (135') passage therethrough. The third pair (103/103') of upstanding feet are at reduced spacing $T_2$ from each other, wherein $T_2$ is less than the diameter of stabilizing rod 135 thus enabling entry of feet 103/103' into an axially locating circumferential groove 139 in rod 135; the thickness $T_3$ of feet 103/103' has sufficient match to the axial extent of groove 139 to permit a sliding precision fit to groove 139 and to provide a well located positioning of groove 139 with respect to the lower or distal end of the outrigger structure 165.

It will be seen that legs 103/103' have a fixed offset from the two pairs 101/101', 102/102' which engage the distal end of the outrigger; in FIG. 15, the dimension X will be understood to designate this fixed offset. It will further be understood that the dimension X, although fixed, is nevertheless specifically related to the radius R of the intramedullary nail 113 with which stabilizer rod 135 and spacer element 100 are to be used, for a guarantee of drill-guide (131) alignments with holes 160/160' when nail 113 is abutted by the distal end 138 of rod 135. Thus, as in the case of spacer 40 of FIG. 11, the spacer 100 of FIGS. 13 to 15 is unique to a particular nail diameter (2R), and permanent indicia of the particular nail diameter are preferably inscribed on each spacer 100 of a plurality to serve a range of nail diameters.

Assembly of the stabilizer system of FIGS. 14 and 15 first involves insertion of the guide sleeve 135' in the precision bore of the distal end of the outrigger; a set screw 104 enables releasable retention of this assembly. Next, stabilizer rod 135 is inserted into guide sleeve 135'. Finally, the spacer element 100 is applied to the distal end of the outrigger, the stabilizer rod 135 being manipulated as necessary to assure locating engagement of feet 103/103' in groove 139. Spring detents 105 (in leg 101') and 106 (in leg 103') respectively engage guide sleeve 135' and the bottom of groove 139 to releasably retain spacer-100 assembly to the outrigger.

In FIG. 13, the clamp bolts 132 are shown on spaced axes that symmetrically straddle the vertical axis of the drill guide 131', thus assuring that the reduced end 138 of the stabilizer rod will contact nail 113 in the geometric plane which is defined by the axis of nail hole 160' and the stabilizer-rod axis. This is a geometric plane of symmetry dividing the entire outrigger structure, perpendicular to the plane of symmetry defined by jig bar 126, nail 113 and the nail holes 160/160'. It will be understood that by thus providing the means to establish accurate drilling of bone on the axis of hole 160', the accurate drilling of bone on the axis of hole 160 is achievable without further set-up or manipulation, in view of the relatively close proximity of axes of holes 160/160' to each other. And it will be further understood that simple unthreading removal of bolts 132 will release the entire outrigger/stabilizer assembly for reversible application with respect to the opposite side of the geometric plane of jig bar 126 and the nail-hole axes to be accessed by drilling via drill guides 131/131'.

What is claimed is:

1. In combination, an intramedullary nail having one or more transverse bone-screw holes, and a drill jig for use in mechanically aligning a drill guide with one or more of said transverse bone-screw holes after the intramedullary nail has been installed in a fractured femur, (i) wherein the intramedullary nail is axially straight and has a proximal end adapted for jig attachment and (ii) wherein said one or more bone-screw holes are in an elongate distally extending portion, said one or more holes and the axis of said nail defining a first geometric plane of symmetry;

said jig comprising elongate straight guide-bar structure of constant non-circular section, and a handle having means for keyed selective connection to the proximal end of the nail such that said handle extends transversely of the nail and in said first geometric plane, said handle having a guide for said guide bar and for retaining said guide-bar structure in said first geometric plane and parallel to said nail, said guide-bar structure having one or more drill-guide bores in general alignment with said one or more holes;

outrigger structure removably carried by said guide-bar structure and extending laterally outboard of said geometric plane of symmetry and having an outer end with a guide bore in a second geometric plane which includes the axis of said nail and is perpendicular to said first plane of symmetry; and a spacer rod adapted for mounting to the guide bore of said outrigger structure and of such effective projecting length from said outrigger structure as to contact said nail when the one or more drill-guide bores of said guide-bar structure are truly aligned with the one or more holes of said nail.

2. The combination of claim 1, in which the nail is of circular section having a known radius, and in which the mounting of said spacer rod to said guide bar includes provision for determining the effective projecting length thereof in accordance with the known radius of the nail.

3. The combination of claim 1, in which the nail is of circular section having a known radius, and in which said rod has a shoulder for limiting said effective projecting length, and means including a spacer selectively engageable to said outrigger structure and engageable by said shoulder at predetermined offset from outrigger engagement, wherein the spacer is one of a plurality of spacers providing different predetermined offsets that are related to different section radii of available nails.

4. The combination of claim 3, in which said spacer comprises a body having first means for removable engagement with and locating reference to said outrigger, said body extending in offset from said first removable-engagement means to a second means of removable engagement with and locating reference to said shoulder.

5. The combination of claim 4, in which said spacer and said first and said second removable-engagement means are integral formations with said body.

6. The combination of claim 4, in which said shoulder is part of a circumferentially continuous groove having spaced walls configured for locating engageability with said second removable-engagement means.

7. The combination of claim 1, in which said guide-bar structure has two longitudinally spaced parallel guide-pin bores in said plane of symmetry, and in which said outrigger structure has two fixed parallel guide pins for assembled orientation of the outrigger structure to the guide-bar structure via said guide-pin bores.

8. The combination of claim 1, in which said guide-bar structure is adjustably securable to said handle at predetermined longitudinal locations coordinated with intramedullary nail length dimensions, such that upon selection of the correct location for a particular nail-length dimension, the mounting of the outrigger structure to the guide-bar structure will always correctly longitudinally position the one or more drill-guide bores in alignment with the one or more bone-screw holes of the intramedullary nail.

9. The combination of claim 1, in which said outrigger structure is symmetrical about said second geometric plane, and in which said outrigger structure includes releasable means for securing the same to said guide-bar structure, said releasable means being also symmetrical about said second geometric plane, whereby said outrigger structure can be selectively and reversibly secured to said guide-bar structure on either side of said first geometric plane.

10. In combination, an intramedullary nail and a drill jig for use in aligning at least one drill guide with a transverse bone-screw hole in the intramedullary nail, wherein the intramedullary nail is straight and has (i) a proximal end adapted for keyed jig attachment and (ii) a elongate distally extending portion of circular section of known radius having the bone-screw hole;

same jig comprising an elongate guide bar and a handle extending transversely from a proximal portion of said bar, said handle having means for keyed selective connection to and rotary orientation of the intramedullary nail, said last-mentioned means establishing a distally extending nail-connection axis which is spaced from and parallel to said guide bar, whereby the guide bar and the distal region of the nail-connection axis define a geometric plane;

an outrigger connected to a distal portion of said guide bar and providing an offset outrigger portion extending to a location of lateral offset from said geometric plane;

first guide means on the laterally offset portion of said outrigger and establishing a first guide-axis orientation perpendicular to said geometric plane and to the distal region of the nail-connection axis, and second guide means on a portion of said guide bar and establishing a second guide-axis orientation contained in said geometric plane and perpendicular to the nail-connection axis;

the keyed connection of said handle orienting the axis of the bone-screw hole for alignment with one of said guide means, and said one of said guide means being adapted for alignment of a drill guide and a spacer rod removably connected to and oriented by the other of said guide means, said spacer rod having a distally offset nail-contactable end which is spaced by a predetermined radial offset from the nail-connection axis, the distal offset being selected to accord with the radius of said intramedullary nail, whereby to assure alignment of the drill guide with the bone-screw hole when said spacer rod is in contact with the intramedullary nail.

11. The method of using a drill jig for mechanically aligning at least one drill guide with a transverse bone-screw hole in an axially extending intramedullary nail that is to be installed in a fractured femur, (i) wherein the intramedullary nail is straight and has a proximal-end portion for selective jig attachment, (ii) wherein said bone-screw hole is in an elongate distally extending portion and defines with the axis of the nail a first geometric plane, and (iii) wherein said jig comprises (a) an elongate bar and (b) a bar-positioning handle having means for keyed selective connection to the nail such that said handle extends transversely of the nail and positions said bar parallel to said distally extending portion, an outrigger carried by said bar in proximity to the bone-screw hole, and first and second guide bores on said bar and on said outrigger, one of said guide bores being aligned perpendicular to and defining with the nail a second geometric plane which is perpendicular to said first geometric plane; said method comprising the steps of:

(1) assembling the drill jig to the intramedullary nail prior to nail installation in the fractured femur;

(2) selecting and mounting a spacer rod with jig-limited guide-bore mounting in said second geometric plane, the spacer-rod selection being such as to provide nail-axis and nail-hole alignment and containment in said first geometric plane, in the circumstance of spacer-rod contact with the intramedullary nail;

(3) checking said assembly for fidelity of said alignment with the mounted spacer rod in a first-established contact with the intramedullary nail;

(4) at least partially disassembling the drill jig to the extent of removing said spacer rod from its mounting;

(5) installing the intramedullary nail in the fractured femur, and then reassembling the jig to the intramedullary nail;

(6) surgically locally exposing the femur and drilling the femur to the extent of nail exposure for spacer-rod contact, and mounting the spacer rod for re-established contact with the nail;

(7) surgically locally exposing the femur and drilling a bore in the femur on the alignment of said other guide bore; and (8) installing a bone screw through the drilled bore, with bone-screw location in the bone-screw hole of the intramedullary nail.

12. The method of using a drill jig for mechanically aligning at least one drill guide with a transverse bone-screw hole in an axially extending intramedullary nail that is to be installed in a fractured femur, (i) wherein the intramedullary nail is straight and has a proximal-end portion for selective jig attachment, (ii) wherein said bone-screw hole is in an elongate distally extending portion of said intramedullary nail and defines with the axis of the nail a first geometric plane, and (iii) wherein said jig comprises (a) an elongate bar and (b) a bar-positioning handle having means for keyed selective connection to the nail such that said handle extends transversely of the nail and positions said bar parallel to said distally extending portion, an outrigger carried by said bar in proximity to the bone-screw hole, a first guide bore on said bar and a second guide bore on said outrigger, one of said guide bores being aligned perpendicular to and defining with the nail a second geometric plane which is perpendicular to said first geometric plane; said method comprising the steps of:

(1) installing the intramedullary nail in the fractured femur, and assembling the jig to the proximal-end portion of the intramedullary nail;

(2) surgically locally exposing the femur and drilling the femur to the extent of nail exposure on the alignment of one of said guide bores;

(3) selecting and mounting a spacer rod to said jig and in contact with the nail and in alignment with said one of said guide bores, the spacer-rod selection being for an effective spacer-rod offset which, with the mounted spacer rod in contact with the nail, has been predetermined to align the other of said guide bores with the bone-screw hole of the nail;

(4) surgically locally exposing the femur on the alignment of the other of said guide bores, and maintaining the mounted spacer rod in contact with the nail while drilling a bore in the femur on the alignment of said other of said guide bores; and (5) installing a bone screw through the drilled bore step (4), with bone-screw location in the bone-screw hole of the intramedullary nail.

13. In combination, an intramedullary nail having one or more transverse bone-screw holes, and a drill jig for use in mechanically aligning a drill guide with one or more of said transverse bone-screw holes after the intramedullary nail has been installed in a fractured tibia, wherein the intramedullary nail has (i) a proximal end adapted for jig attachment and (ii) a single bent portion near said proximal end and (iii) a straight remaining elongate portion extending distally of said bent portion and having said one or more holes, whereby a sagittal plane of symmetry is defined by said bent and remaining portions;

said jig comprising an elongate guide bar of constant non-circular section, and a handle having means for keyed selective connection to the proximal end of the nail such that said handle extends transversely of the nail and in said sagittal plane, said handle having a guide for said guide bar for retaining said guide bar in said sagittal plane of the nail and parallel to said elongate remaining portion of the nail;

outrigger structure removably carried by said guide bar and extending laterally outboard of said sagittal plane and having an outer end with one or more drill-guide bores in general alignment with said one or more holes; and a spacer rod adapted for removable mounting to said guide bar in the sagittal plane of the nail and near said outrigger structure and of such length as to contact said nail when the one or more drill-guide bores of said outrigger structure are truly aligned with the one or more holes of said nail.

14. The combination of claim 13, in which the bone-screw holes of the nail are on axes normal to the sagittal plane of the nail, and in which the one or more drill-guide bores of said outrigger structure are also on axes normal to the sagittal plane of the nail.

15. The combination of claim 13, in which the nail is of circular section having a known radius, and in which the mounting of said spacer rod to said guide bar includes provision for determining the effective length thereof in accordance with the known radius of the nail.

16. The combination of claim 13, in which the nail is of circular section having a known radius, and in which said guide bar has a guide bore for inserted orientation of said spacer rod in the sagittal plane of the nail, said rod having a shoulder for limiting the extent of rod projection toward the nail, and means including a shim selectively applicable to the guide bar and engageable by said shoulder, wherein the shim is one of a plurality of shims of different thickness that is related to different section radii of available nails.

17. The combination of claim 13, in which said guide bar has two longitudinally spaced parallel guide-pin bores in the sagittal plane of the nail, and in which said outrigger structure has two fixed parallel guide pins for assembled orientation of the outrigger structure to the guide bar via said guide-pin bores.

18. The combination of claim 13, in which the outrigger structure extends to a single lateral and downward offset with respect to the guide bar and with respect to the sagittal plane such that the drill-guide bores of said outrigger structure are perpendicular to said sagittal plane.

19. The combination of claim 13, in which the guide bar is adjustably securable to said handle at predetermined longitudinal locations coordinated with intramedullary nail length dimensions, such that upon selection of the correct location for a particular nail-length dimension, the mounting of the outrigger structure to the guide bar will always correctly longitudinally position the one or more drill-guide bores in alignment with the one or more bone-screw holes of the intramedullary nail.

20. The combination of claim 13, in which the bone-screw holes of the intramedullary nail are at longitudinal spacing and at equal and opposite angles of incidence with the sagittal plane of the nail, and in which said outrigger structure extends to opposing lateral and downward offsets of its respective ends with respect to the sagittal plane of the nail, there being at least one drill-guide bore at each of the offset ends of the outrigger structure, such that the axis of each of the respective drill-guide bores is aligned with a different one of the bone-screw holes of the nail.

21. The combination of claim 20, in which said guide bar has two longitudinally spaced guide-pin bores in the sagittal plane of the nail, and in which said outrigger structure has two fixed parallel guide pins for assembled orientation of the outrigger structure to the guide bar via said guide-pin bores.

22. The combination of claim 13, in which the nail is of circular section having known radius, and in which said guide bar has a guide bore for inserted orientation of said spacer rod in the sagittal plane of the nail, said spacer rod having two spaced circumferential grooves, a U-shaped fitting adapted to fit to one side of the guide bar, with opposite legs of the U-shape lapping upper and lower limits of the cross-section of the guide bar, said legs being slotted to define spaced fork elements which are enterable in the spaced grooves of the spacer rod whereby to limit spacer-rod approach to the intramedullary nail, the thickness of one of the legs of the U-shaped fitting being of predetermined relation to the known section radius of the intramedullary nail such that, when the spacer rod is urged in the direction of spacer-rod contact with the intramedullary nail, the contact will be such as to determine correct alignment of the one or more drill-guide bores with the one or more bone-screw holes of the intramedullary nail.

23. In combination, an intramedullary nail having two spaced parallel transverse bone-screw holes, and a drill jig for use in mechanically aligning two correspondingly spaced parallel drill guides with said two spaced transverse bone-screw holes after said intramedullary nail has been installed in a fractured elongate bone, wherein the intramedullary nail has (i) a proximal-end portion adapted for jig attachment and (ii) a straight elongate distally extending portion having said bone-screw holes, whereby a sagittal plane of symmetry is defined by said straight portion and by a normal to a geometric plane containing the axis of each of said bone-screw holes;

said jig comprising an elongate guide bar of constant non-circular section, and a handle having means for keyed selective connection to the proximal end of the nail such that said handle extends transversely of the nail and in said sagittal plane, said handle having a guide for said guide bar for retaining said guide bar in said sagittal plane of the nail and parallel to said elongate portion of the nail;

outrigger structure removably carried by said guide bar and extending laterally outboard of said sagittal plane and having an outer end with one or more drill-guide bores in general alignment with said one or more holes; and a spacer rod adapted for removable mounting to said guide bar in the sagittal plane of the nail and near said outrigger structure and of such length as to contact said nail when the one or more drill-guide bores of said outrigger structure are truly aligned with the one or more holes of said nail.

24. In combination, an intramedullary nail having two spaced parallel vertically extending bone-screw holes, and a drill jig for use in mechanically aligning a drill guide with one or both of said vertical bone-screw holes after said intramedullary nail has been installed in a fractured tibia, wherein the intramedullary nail has (i) a proximal end adapted for jig attachment and (ii) a single bent portion near said proximal end and (iii) a straight remaining elongate portion extending distally of said bent portion and having said two vertical bone-screw holes, whereby a sagittal plane of symmetry is defined by said bent and remaining portions and by said vertical bone-screw holes;

said jig comprising an elongate guide bar of constant non-circular section, and a handle having means for keyed selective connection to the proximal end of the nail such that said handle extends transversely of the nail and in said sagittal plane, said handle having a guide for said guide bar for longitudinally selected retention of said guide bar in said sagittal plane and parallel to said elongate remaining portion of the nail;

a drill guide with at least one drill-guide bore;

means carried by said guide bar near the distal end thereof for removably clamping said drill guide to said bar with the axis of the at least one drill-guide bore in said sagittal plane and perpendicular to the elongate direction of said guide bar, and with the axis of said at least one drill-guide bore longitudinally positioned for alignment with one of said bone-screw holes;

outrigger structure removably carried by said guide bar and extending laterally outboard of said sagittal plane and having an outer end with a mounted spacer rod in an orientation directed toward and perpendicular to the nail and to said sagittal plane, said spacer rod contacting said nail when the one or more drill-guide bores of said guide bar are truly aligned with the one or more bone-screw holes of said nail.

25. The combination of claim 24, in which the nail is of circular section having a known radius, and in which the mounting of said spacer rod to said outrigger includes provision for determining the effective length thereof in accordance with the known radius of the nail.

26. The combination of claim 24, in which the nail is of circular section having a known radius, and in which said outrigger has a guide bore for inserted orientation of said spacer rod perpendicular to the sagittal plane of the nail, said rod having a shoulder for limiting the extent of rod projection toward the nail, and means including a shim selectively applicable to said outrigger and engageable by said shoulder, wherein the shim is one of a plurality of shims of different thickness that is related to different section radii of available nails.

27. The combination of claim 24, in which said guide bar has two longitudinally spaced parallel guide-pin bores in the sagittal plane of the nail, and in which said outrigger structure has two fixed parallel guide pins for assembled orientation of the outrigger structure to the guide bar via said guide-pin bores.

28. The combination of claim 24, in which the bone-screw holes of the intramedullary nail are at longitudinal spacing and at equal and opposite angles of incidence with the sagittal plane of the nail, and in which said outrigger structure extends to opposing lateral and downward offsets of its respective ends with respect to the sagittal plane of the nail, there being at least one drill-guide bore at each of the offset ends of the outrigger structure, such that the axis of each of the respective drill-guide bores is aligned with a different one of the bone-screw holes of the nail.

29. The combination of claim 28, in which said guide bar has two longitudinally spaced guide-pin bores in the sagittal plane of the nail, and in which said outrigger structure has two fixed parallel guide pins for assembled orientation of the outrigger structure to the guide bar via said guide-pin bores.

30. In combination, an intramedullary nail of circular section having known radius and having two spaced parallel vertically extending bone-screw holes, and a drill jig for use in mechanically aligning a drill guide with one or both of said vertical bone-screw holes after said intramedullary nail has been installed in a fractured tibia, wherein the intramedullary nail has (i) a proximal end adapted for jig attachment and (ii) a single bent portion near said proximal end and (iii) a straight remaining elongate portion extending distally of said bent portion and having said two vertical bone-screw holes, whereby a sagittal plane of symmetry is defined by said bent and remaining portions and by said vertical bone-screw holes;

said jig comprising an elongate guide bar of constant non-circular section, and a handle having means for keyed selective connection to the proximal end of the nail such that said handle extends transversely of the nail and in the sagittal plane thereof, said handle having a guide for said guide bar for retaining said guide bar in the sagittal plane of the nail and parallel to said elongate remaining portion of the nail;

means carried by said guide bar near the distal end thereof for removably clamping at least one drill guide to said bar with the axis of the drill guide in said sagittal plane and perpendicular to the elongate direction of said guide bar;

outrigger structure removably carried by said guide bar and extending laterally outboard of said sagittal plane and having an outer end with means for selectively mounting a spacer rod in an orientation directed toward and perpendicular to the nail and to said sagittal plane, the spacer rod being of such length as to contact said nail when the one or more drill-guide bores of said guide bar are truly aligned with the one or more bone-screw holes of said nail;

said outrigger structure having a guide bore for inserted orientation of said spacer rod perpendicular to the sagittal plane of the nail, said spacer rod having two spaced circumferential grooves, a U-shaped fitting adapted to fit one side of the outrigger with opposite legs of the U-shape lapping opposite limits of the cross-section of the outrigger, said legs being slotted to define spaced fork elements which are enterable in the spaced grooves of the spacer rod whereby to limit spacer-rod approach to the intramedullary nail, the thickness of one of the legs of the U-shaped fitting being of predetermined relation to the known section radius of the intramedullary nail such that, when the spacer rod is urged in the direction of spacer-rod contact with the intramedullary nail, the contact will be such as to determine correct alignment of the one or more drill-guide bores with the one or more bone-screw holes of the intramedullary nail.

31. In combination, an elongate intramedullary nail having two longitudinally spaced parallel transverse bone-screw holes, and a drill jig for use in mechanically aligning two correspondingly spaced parallel drill guides with said two spaced bone-screw holes after the intramedullary nail has been installed in a fractured elongate bone, the intramedullary nail having (i) a proximal end adapted for jig attachment and (ii) a straight elongate distally extending portion having said bone-screw holes, whereby a sagittal plane of symmetry is defined by said straight portion and by the axis of each of said bone-screw holes;

said jig comprising an elongate guide bar of constant non-circular section, and a handle having means for keyed selective connection to the proximal end of the nail such that said handle extends transversely of the nail and in the sagittal plane thereof, said guide bar having two spaced parallel drill-guide bores at the spacing of the bone-screw holes of the intramedullary nail, and said handle having a guide for said guide bar for retaining said guide bar in the sagittal plane of the nail and parallel to said elongate portion of the nail;

outrigger structure removably carried by said guide bar near the drill-guide bores and extending laterally outboard of said sagittal plane and having an outer end with means for supporting an elongate spacer rod in an orientation directed to the intramedullary nail and perpendicular to said sagittal plane; and a spacer rod for mounting to said outrigger in perpendicular relation to the sagittal plane of the nail and contacting said nail when the one or more drill-guide bores of said guide bar are truly aligned with the bone-screw holes of said nail.

32. The combination of claim 31, in which the nail is of circular section having a known radius, and in which said outrigger has a guide bore for inserted orientation of said spacer rod perpendicular to the sagittal plane of the nail, said rod having a shoulder for limiting the extent of rod projection toward the nail, and means including a shim selectively applicable to said outrigger and engageable by said shoulder, wherein the shim is one of a plurality of shims of different thickness that is related to different section radii of available nails.

33. In combination, an elongate intramedullary nail having two spaced transverse bone-screw holes, and a drill jig for use in mechanically aligning two correspondingly spaced parallel drill guides with said two spaced bone-screw holes after the intramedullary nail has been installed in a fractured elongate bone, the intramedullary nail having (i) a proximal end adapted for jig attachment and (ii) a straight elongate distally extending portion having said bone-screw holes;

said jig comprising an elongate guide bar of constant non-circular section, and a handle having means for keyed selective connection to the proximal end of the nail, such that said handle extends transversely of the nail, said handle positioning said guide bar in spaced parallel relation to said distally extending portion of the nail, whereby said distally extending portion of the nail and said guide bar define a geometric plane;

an outrigger and means for detachably connecting said outrigger to said guide bar such that the remainder of said outrigger extends to a location of offset from said geometric plane;

first guide means on a portion of the remainder of said outrigger and establishing a guide-axis orientation perpendicular to said geometric plane and to said distally extending portion of the nail, and second guide means on a portion of said guide bar and establishing a guide-axis orientation perpendicular to said distally extending portion of the nail, the guide axis orientation of said second guide means being contained in said geometric plane, one of said guide means being for alignment of two spaced drill guides with the respective bone-screw holes of the nail; and a nail-contactable spacer rod removably engaged to and aligned with the other of said guide means for spacer-rod contact with the nail at a location which is longitudinally offset from said one guide means, said spacer rod contacting the nail when said two spaced drill guides are truly aligned with the bone-screw holes of said nail.

34. In combination, an elongate intramedullary nail having at least one transverse bone-screw hole, and a drill jig for use in mechanically aligning at least one drill guide with a transverse bone-screw hole in said intramedullary nail after said nail has been installed in a fractured elongate bone, the intramedullary nail having (i) a proximal end adapted for jig attachment and (ii) a straight elongate distally extending portion having said bone-screw hole;

said jig comprising an elongate guide bar of constant non-circular section, and a handle having means for keyed selective connection to the proximal end of the nail, such that said handle extends transversely of the nail, said handle positioning said guide bar in spaced parallel relation to the distally extending portion of the nail, whereby the nail and said guide bar define a geometric plane;

an outrigger and means for detachably connecting a portion of said outrigger to said guide bar such that an offset portion of the remainder of said outrigger extends to a location of offset from said geometric plane;

first guide means on a portion of the remainder of said outrigger and establishing a guide-axis orientation perpendicular to said geometric plane and to said distally extending portion of the nail, and second guide means on a portion of said guide bar and establishing a guide-axis orientation perpendicular to said distally extending portion of the nail, the guide axis orientation of said second guide means being contained in said geometric plane;

one of said guide means being adapted for alignment of a drill guide with the bone-screw hole, a nail-contactable spacer rod adapted for aligned engagement with the other of said guide means, and said other guide means being adapted for alignment of said nail-contactable spacer rod with the nail at a location which is in longitudinal proximity to said first guide means.

35. In combination, an elongate intramedullary nail having at least one transverse bone-screw hole, and a drill jig for use in mechanically aligning at least one drill guide with a transverse bone-screw hole in said intramedullary nail after said nail has been installed in a fractured elongate bone, the intramedullary nail having (i) a proximal end adapted for jig attachment and (ii) a straight elongate distally extending portion having said bone-screw hole;

said jig comprising an elongate guide bar of constant non-circular section, and a handle having means for keyed selective connection to the proximal end of the nail, such that said handle extends transversely of the nail, said handle positioning said guide bar in spaced parallel relation to the distally extending portion of the nail, whereby the nail and said guide bar define a geometric plane;

an outrigger and means for detachably connecting a portion of said outrigger to said guide bar such that an offset portion of the remainder of said outrigger extends to a location of offset from said geometric plane;

first guide means on a portion of the remainder of said outrigger and establishing a guide-axis orientation perpendicular to said geometric plane and to said distally extending portion of the nail, and second guide means on a portion of said guide bar and establishing a guide-axis orientation perpendicular to said distally extending portion of the nail, the guide axis orientation of said second guide means being contained in said geometric plane;

one of said guide means being adapted for alignment of a drill guide with the bone-screw hole, and the other of said guide means being adapted for alignment of a nail-contactable spacer rod with the nail at a location which is in longitudinal proximity to said first guide means;

the bone-screw hole being on an axis in close parallel adjacency to said geometric plane, and the drill-guide alignment of said one guide means being in said close parallel adjacency to said geometric plane, a spacer rod guided by the other of said guide means, and stop means coacting between said spacer rod and said offset portion of said outrigger for determining a precise nail-contacting location of offset of the nail from said offset portion of said outrigger, said nail-contacting location being predetermined for positioning assurance of the bone-screw hole axis in said geometric plane.

36. In combination, an elongate intramedullary nail having at least one transverse bone-screw hole, and a drill jig for use in mechanically aligning at least one drill guide with a transverse bone-screw hole in said intramedullary nail after said nail has been installed in a fractured elongate bone, the intramedullary nail having (i) a proximal end adapted for jig attachment and (ii) a straight elongate distally extending portion having said bone-screw hole;

said jig comprising an elongate guide bar of constant non-circular section, and a handle having means for keyed selective connection to the proximal end of the nail, such that said handle extends transversely of the nail, said handle positioning said guide bar in spaced parallel relation to the distally extending portion of the nail, whereby the nail and said guide bar define a geometric plane;

an outrigger and means for detachably connecting a portion of said outrigger to said guide bar such that an offset portion of the remainder of said outrigger extends to a location of offset from said geometric plane;

first guide means on a portion of the remainder of said outrigger and establishing a guide-axis orientation perpendicular to said geometric plane and to said distally extending portion of the nail, and second guide means on a portion of said guide bar and establishing a guide-axis orientation perpendicular to said distally extending portion of the nail, the guide axis orientation of said second guide means being contained in said geometric plane;

one of said guide means being adapted for alignment of a drill guide with the bone-screw hole, and the other of said guide means being adapted for alignment of a nail-contactable spacer rod with the nail at a location which is in longitudinal proximity to said first guide means;

the bone-screw hole being on an axis perpendicular to said geometric plane, and the drill-guide alignment of said one guide means being perpendicular to said geometric plane, a spacer rod guided by the other of said guide means, and stop means coacting between said spacer rod and said guide bar for determining a precise nail-contacting location of spacing of the nail from said guide bar, said nail-contacting location being pre-determined for positioning assurance of the bone-screw hole axis in alignment with the bone-screw hole.

37. The method of using a drill jig for mechanically aligning at least one drill guide with a transverse bone-screw hole in an intramedullary nail that is to be installed in a fractured bone, wherein the intramedullary nail has (i) a proximal-end portion for selective jig attachment and (ii) a straight elongate distally extending portion having said bone-screw hole, and wherein said jig comprises (a) an elongate bar and (b) a bar-positioning handle having means for keyed selective connection to the nail such that said handle extends transversely of the nail and positions said bar parallel to said distally extending portion, an outrigger carried by said bar in proximity to the bone-screw hole, first and second guide bores on said bar and on said outrigger, one of said guide bores being aligned perpendicular to and defining with the nail a first geometric plane which is to include the bone-screw hole, and the other of said guide bores being aligned perpendicular to and defining with the nail a second geometric plane which is perpendicular to said first geometric plane; said method comprising the steps of:

(1) assembling the drill jig to the intramedullary nail prior to nail installation in the fractured bone;

(2) selecting and positioning a spacer rod for outrigger-limited guide-bore mounting in said second geometric plane and for spacer-rod contact with the nail, such that said spacer rod determines nail-axis and nail-hole axis alignment and containment in said first geometric plane;

(3) at least partially disassembling the drill jig to the extent of removing said spacer rod from its mounting;

(4) installing the intramedullary nail in the fractured bone, with the jig re-assembled thereto;

(5) surgically exposing and drilling bone in the region of spacer-rod contact and mounting the spacer rod for re-established contact with the nail;

(6) maintaining outrigger-limited spacer contact with the nail;

(7) surgically exposing and drilling a bore in bone on the alignment of said other guide bore; and (8) installing a bone screw through the drilled bore, with bone-screw location in the bone-screw hole of the intramedullary nail.

38. The method of using a drill jig for mechanically aligning at least one drill guide with a transverse bone-screw hole in an intramedullary nail that is to be installed in a fractured bone, wherein the intramedullary nail has (i) a proximal-end portion for selective jig attachment and (ii) a straight elongate distally extending portion having said bone-screw hole, and wherein said jig comprises (a) an elongate bar and (b) a bar-positioning handle having means for keyed selective connection to the nail such that said handle extends transversely of the nail and positions said bar parallel to said distally extending portion, an outrigger carried by said bar in proximity to the bone-screw hole, first and second guide bores on said bar and on said outrigger, one of said guide bores being aligned perpendicular to and defining with the nail a first geometric plane which is to include the bone-screw hole, and the other of said guide bores being aligned perpendicular to and defining with the nail a second geometric plane which is perpendicular to said first geometric plane; said method comprising the steps of:

(1) assembling the drill jig to the intramedullary nail prior to nail installation in the fractured bone;

(2) selecting and positioning a spacer rod for bar-limited guide-bore mounting in said first geometric plane and for spacer-rod contact with the nail, such that said spacer rod determines nail-axis and nail-hole axis alignment and containment in said second geometric plane;

(3) at least partially disassembling the drill jig to the extent of removing said spacer rod from its mounting;

(4) installing the intramedullary nail in the fractured bone, with the jig re-assembled thereto;

(5) surgically exposing and drilling bone in the region of spacer-rod contact and mounting the spacer rod for re-established contact with the nail;

(6) maintaining bar-limited spacer contact with the nail;

(7) surgically exposing and drilling a bore in bone on the alignment of said other guide bore; and (8) installing a bone screw through the drilled bore, with bone-screw location in the bone-screw hole of the intramedullary nail.

39. The method of using a drill jig for mechanically aligning at least one drill guide with a transverse bone-screw hole in an intramedullary nail that is to be installed in a fractured tibia, wherein the intramedullary nail has (i) a proximal-end portion for selective jig attachment and (ii) a straight elongate distally extending portion having said bone-screw hole, and wherein said jig comprises (a) an elongate bar and (b) a bar-positioning handle having means for keyed selective connection to the nail such that said handle extends transversely of the nail and positions said bar parallel to said distally extending portion, an outrigger carried by said bar in distal-end proximity to the bone-screw hole, first and second guide bores on said bar and on said outrigger, one of said guide bores being aligned perpendicular to and defining with the nail a first geometric plane which is to include the bone-screw hole, and the other of said guide bores being aligned perpendicular to and defining with the nail a second geometric plane which is perpendicular to said first geometric plane; said method comprising the steps of:

(1) assembling the drill jig to the intramedullary nail prior to nail installation in the fractured tibia;

(2) selecting and positioning a spacer rod for bar-limited guide-bore mounting in said first geometric plane and for spacer-rod contact with the nail, such that said spacer rod determines nail-axis and nail-hole axis alignment and containment in said second geometric plane;

(3) at least partially disassembling the drill jig to the extent of removing said spacer rod from its mounting;

(4) installing the intramedullary nail in the fractured tibia, the jig being reassembled thereto;

(5) surgically locally exposing the tibia and drilling the tibia to the extent of nail exposure in the region of spacer-rod contact, and mounting the spacer rod for re-established contact with the nail;

(6) maintaining bar-limited spacer contact with the nail;

(7) surgically exposing the tibia and drilling a bore in the tibia on the alignment of said other guide bore; and (8) installing a bone screw through the drilled bore, with bone-screw location in the bone-screw hole of the intramedullary nail.

40. In combination, an intramedullary nail extending between a distal bone-entry end and a proximal jig-connectable end and having at least one transverse bone-screw hole in an axially straight portion between said ends, and a drill jig having a drill-guide bore for use in mechanically aligning a drill guide with said bone-screw hole after installation of the intramedullary nail in a fractured bone;

said jig comprising an elongate guide bar, a handle connected to said guide bar and having means for keyed removable connection to the proximal end of the nail such that said handle extends transversely of the nail and said guide bar is in spaced parallel relation to the axially straight portion of the intramedullary nail to establish a geometric plane of symmetry wherein the bone-screw hole is normal to the geometric plane;

said jig further comprising outrigger structure removably carried by the guide bar and extending laterally outboard of the geometric plane and having an outer end with the drill-guide bore in general alignment with the bone-screw hole; and a spacer rod adapted for mounting to said guide bar in said geometric plane and near said outrigger structure and of such length as merely to tangentially contact the axially straight portion of said nail when the drill-guide bore of said outrigger structure is truly aligned with the bone-screw hole of said nail.

41. In combination, an intramedullary nail extending between a distal bone-entry end and a proximal jig-connectable end and having at least one transverse bone-screw hole in an axially straight portion between said ends, and a drill jig having a drill-guide bore for use in mechanically aligning a drill guide with said bone-screw hole after installation of the intramedullary nail in a fractured bone;

said jig comprising an elongate guide bar, a handle connected to said guide bar and having means for keyed removable connection to the proximal end of the nail such that said handle extends transversely of the nail and said guide bar is in spaced parallel relation to the axially straight portion of the intramedullary nail to establish a geometric plane of symmetry wherein the axis of the bone-screw hole is in the geometric plane, and wherein the drill-guide bore is in said guide bar on an axis in said geometric plane and perpendicular to the intramedullary nail and in general alignment with the bone-screw hole;

said jig further comprising outrigger structure removably carried by the guide bar and extending laterally outward of said geometric plane and having an outer end with another guide bore oriented perpendicular to said geometric plane and to the intramedullary nail; and a spacer rod adapted for mounting to the outer end of said outrigger via said other guide bore, and said spacer rod tangentially contacting the axially straight portion of said nail when the drill-guide bore of said outrigger structure is truly aligned with the bone-screw hole of said nail.

* * * * *

UNITED STATES PATENT AND TRADEMARK OFFICE
CERTIFICATE OF CORRECTION

PATENT NO.    : 5,620,449
DATED         : April 15, 1997
INVENTOR(S)   : Giovanni FACCIOLI, ET AL.

It is certified that error appears in the above-indentified patent and that said Letters Patent is hereby corrected as shown below:

| | |
|---|---|
| Column 3, line 9; | after "FIG. 12", delete "ms" and insert therefor --is-- |
| Column 6, line 49; | delete "NAIL ϕ9" and insert therefor -- "NAIL ø9" -- after "NAIL ϕ9", delete "0" |
| Column 12, line 39; | before "jig" delete "same" and insert therefor --said-- |
| Column 12, line 63; | after "drill guide" insert a semicolon --;-- |
| Column 14, lines 19 & 20; | before "step (4)" insert --of-- |

Signed and Sealed this

Thirty-first Day of March, 1998

Attest:

BRUCE LEHMAN

*Attesting Officer*     *Commissioner of Patents and Trademarks*